United States Patent [19]

Johnson, Jr. et al.

[11] Patent Number: Plant 7,171

[45] Date of Patent: Feb. 27, 1990

[54] STRAWBERRY—ANACAPA

[75] Inventors: Harold A. Johnson, Jr.; Thomas M. Sjulin, both of Watsonville; David W. Small, Ventura; Amado Q. Amorao; Joseph I. Espejo, Jr., both of Watsonville, all of Calif.

[73] Assignee: Driscoll Strawberry Associates, Inc., Watsonville, Calif.

[21] Appl. No.: 291,911

[22] Filed: Dec. 29, 1988

[51] Int. Cl.[4] ..... A01H 5/00

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct spring bearing variety of strawberry plant, characterized by its ability to produce large, glossy, dark crown crop berries during the early spring when given adequate chilling before being winter planted in southern California.

It is distinguished by its consistently good shaped fruit that reflect an abundance of pollen production and uniformly fertilized pistil and achenes that develop. This crown crop fruit with its large calyx is borne on long thick pedicils. The plant is considered dark, and is vigorous only if given adequate chilling before being planted. This variety has the ability to continue cropping even in the summer, after the picking for the fresh market has been terminated.

1 Drawing Sheet

DESCRIPTION

This invention relates to a new and distinct variety of strawberry known as 'Anacapa', and which is the result of a cross of 'Joe Reiter', U.S. Plant Pat. No. 5,300 and 'Crown Variety', U.S. Plant Pat. No. 5,301.

The seedlings resulting from the aforementioned cross were grown and asexually multiplied in Shasta County, Calif., and tested in the fruiting beds on the property of member growers of Driscoll Strawberry Associates, Inc. Clones of the seedlings are also held at the Propagation Nursery in Shasta County. One plant was selected from the aforementioned group of seedlings and further asexually reproduced by runners in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Figure 1:
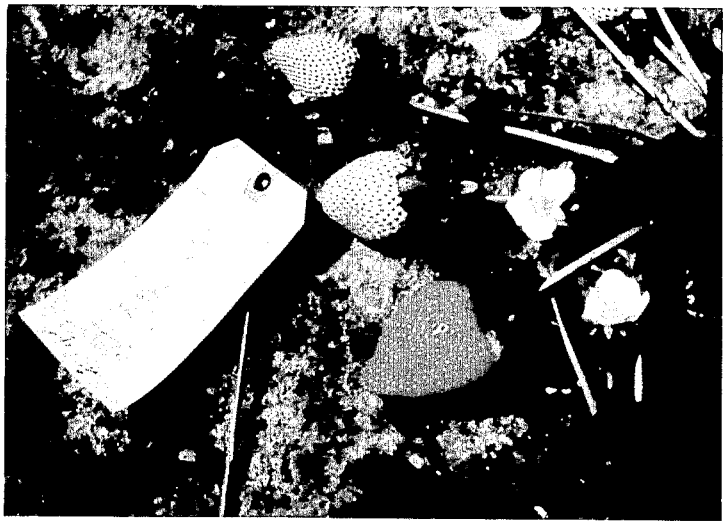
FIG. 1 illustrates plant characteristics and Crown crop fruit typical of the variety grown in Oxnard, Calif.
Figure 2:
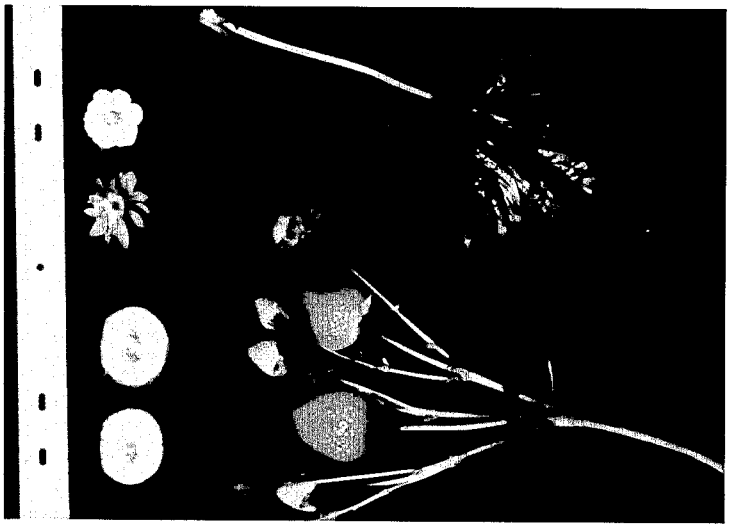
FIG. 2 illustrates the plant parts and ripe primary and secondary berries typical of the new variety grown at Watsonville, Calif.

The two accompanying drawings illustrate plant parts of the new variety. FIG. 1 was photographed on March 24, in Oxnard, Calif., and FIG. 2 was taken in Watsonville, Calif. on May 28. FIG. 1 illustrates fruit and plant parts of the crown crop with the long pedicel of all berries originated from very short peduncles near the crown, so that only pedicels are visible when observing from above the plant. This ripe crown crop berry is large and attractive with a glossy, dark color. Its shape is conic with slightly recessed longitudinal furrows. When observing a berry from the side, it is slightly concave near the apex. Only part of the small dark plant is visible in this picture. The flowers shown are producing visible anthers. FIG. 2 shows plant parts grown at Watsonville on May 28, where a large ripe primary and a ripe secondary are present. The large primary is medium to long conic to slightly wedged at the apex and the secondary is conic in outline as is illustrated in the USDA Bulletin 1043. The light colored flesh and core cavity are visible as well as a typical inflorescence at this time of year in Watsonville. The pedicel holding the primary berry originates from the axil of two secondary peduncles and the ripe secondary originates from the axil of pedicels holding tertiary berries. These pedicels holding primary and secondary pedicels may also originate from peduncles and not axils. The pedicels holding secondary and tertiary fruit opposite the 27 cm mark on the ruler in FIG. 2 are fused together, which is a characteristic that is common. A dark colored leaf is present with rugose leaflets, moderately deep serrations, and a single leaflet bract is present on the petiole. These bracts may or may not be present.

The novel winter planted spring variety is adapted mainly to southern California as its crown crop fruit is large and attractive and its plant is strong, but only if given enough chilling before being planted. It differs from 'Joe Reiter'—U.S. Plant Pat. No. 5,300, in that the 'Joe Reiter' is a lower chilling variety in that less chilling is necessary to develop a strong plant and support its crop. The new variety also differs from 'Joe Reiter' as its plant is darker, lower growing, but may be denser, has more bracts on its petioles and its leaflets are more rugose than the 'Joe Reiter'. The cropping of the 'Anacapa' is similar to that of 'Joe Reiter' with equal production early and late in the season. The fruit size is equal for the season with both varieties capable of producing a large crown crop as well as large main crop berries with a gradual drop in size during the fresh market season. The 'Anacapa' has a larger crown crop and fruit size during the summer in Watsonville. The fruit of the 'Anacapa' is darker, more conic, smoother, has a firmer skin, but not necessarily a better shelf life, and with seed that is more exerted than 'Joe Reiter'. The calyx of both varieties is large and shiny, but the sepals of 'Anacapa' are usually larger and darker when comparing the sepals facing the fruit. When comparing the isozymes in leaf extract, the PG1 of the new variety is A2 as designated by R. Bringhurst, and the 'Joe Reiter' is A4. Both varieties have rated high when subjected to taste panels with 'Anacapa' having more tang, but 'Joe Reiter' slightly sweeter to the taste (Tang denotes a pungent flavor).

Both varieties have the ability to continue cropping in the summer after the termination of marketing for the fresh market. The new variety is equally susceptible to damage due to two-spotted mite and powdery mildew. The strawberry aroma is equal to that of 'Joe Reiter' variety.

Tests have shown that it has a moderate resistance to Botrytis. It has not shown to be susceptible to severe injury to Mycosphaerella leaf spot or the virus carried by strawberry aphids. It has not been tested for resistance to Verticillium wilt and it has not shown susceptibility to *Phytophthora cactorum,* but in laboratory tests, it has proven to be as susceptible as the 'Joe Reiter' and the 'Thomas' variety to *Colletotrichum acutatum.*

The varietal characteristics of the novel plant, described below in detail, were observed mainly during March, April and May in Oxnard, Calif., and May and June in Watsonville, Calif., which are cool coastal areas near the Pacific Ocean. The color terminology is in accordance with the Munsell color system.

*Plant.*—Medium in size as a winter planted variety in southern California. May become dense if given excessive chilling before being planted. Has a medium chilling requirement and is not considered a low chilling variety.

*Leaves.*—Mostly medium in size, central leaflet 6 to 7 cm. Petioles are short to medium in length and lengthen during the fruiting season, and become long in central California. Bracts are often present on petioles. Leaflets are dark and moderately rugosee. Color of leaves are 0.6G 2.8/6.5 to 8.9GY 2.3/4.7 and the isozymes in leaf extracts is PG1-A2, LAP is B3, and PGM is C4 as designated by R. Bringhurst. This testing was done by Driscoll Strawberry Associates Laboratory following the procedure described in publication. "Electrophoretic Characterization of California Strawberry Cultivars" by Bringhurst—1981.

*Runners.*—Runners are vigorous and abundant at the nursery, as well as in the fruiting bed, if given more than correct chilling for maximum fruit production.

*Inflorescence.*—Crown crop pedicels are long and may become 3 mm in thickness, and subsequent complete inflorescences are long with many becoming over 30 cm in length (from crown to fruit apex). When complete inflorescences develop, the pedicel holding the primary berry may originate from an axil of secondary peduncles or an equal amount may originate from a secondary peduncle. The hairs on tertiary pedicels are held irregularly parallel to the pedicel. Pedicels of tertiary berries may be fused to peduncles. The large flower petals are showy and visible away from the plant, but may or may not touch the soil.

*Fruit.*—Both Crown crop and main crop primary fruit are large, 40 to 45 mm in length and width. Until May, in southern California, the average size of all fruit is above 20 gms per berry. The shape is mainly conic to short to medium wedge as described in the USDA Bulletin 1043. Berries are generally smooth and free of malformation. Primaries may have shallow longitudinal furrows and the fruit surface may be slightly concave near the apex as is shown in FIG. 1. The seeds are generally held equal to the skin surface. Both the flesh and skin are firm, but may show shipping injury. The fruit surface is dark and glossy. The color of fruit surface is 6.6R 2.9/9.7 to 5.5R 2.9/11.6. Flesh color varies from 0.5R 4.9/16.6 to 5.8R 8.0/5.4 near the surface to streaks of white at the core. The flavor quality is good becoming succulent with a tang.

*Calyx.*—The calyx is large and showy with the calyx of primaries becoming more than 50 mm. in diameter. Individual sepals of primaries are serrated, but those of secondaries are usually not. The calyx is slightly reflexed, usually not clasping. Color of sepals that face the fruit is 9.8GY 8.1/94 to 5.6GY 2.3/3.6.

We claim:

1. The new and distinct variety of strawberry plant herein described and illustrated and having the characteristics herein enumerated together with the parts thereof.

* * * * *